US011898148B2

(12) United States Patent
Perkins et al.

(10) Patent No.: US 11,898,148 B2
(45) Date of Patent: Feb. 13, 2024

(54) SEQUENTIAL LOADINGS OF MULTIPLE DELIVERY VECTORS USING A SINGLE SELECTABLE MARKER

(71) Applicant: SynPloid Biotek, LLC, Savannah, GA (US)

(72) Inventors: Edward Perkins, Savannah, GA (US); Amy Greene, Savannah, GA (US)

(73) Assignee: CarryGenes Bioengineering, LLC, Savannah, GA (US)

( * ) Notice: Subject to any disclaimer, the term of this patent is extended or adjusted under 35 U.S.C. 154(b) by 985 days.

(21) Appl. No.: 16/092,828

(22) PCT Filed: Apr. 12, 2017

(86) PCT No.: PCT/US2017/027102
§ 371 (c)(1),
(2) Date: Oct. 11, 2018

(87) PCT Pub. No.: WO2017/180684
PCT Pub. Date: Oct. 19, 2017

(65) Prior Publication Data
US 2020/0157553 A1    May 21, 2020

Related U.S. Application Data

(60) Provisional application No. 62/321,711, filed on Apr. 12, 2016.

(51) Int. Cl.
| C12N 15/64 | (2006.01) |
| C12N 15/65 | (2006.01) |
| C12N 15/52 | (2006.01) |
| C12N 15/11 | (2006.01) |

(52) U.S. Cl.
CPC ............ *C12N 15/64* (2013.01); *C12N 15/65* (2013.01)

(58) Field of Classification Search
None
See application file for complete search history.

(56) References Cited

U.S. PATENT DOCUMENTS

| 2002/0160410 A1 | 10/2002 | Hadlaczky et al. | |
| 2004/0096891 A1 | 5/2004 | Bennett | |
| 2005/0181506 A1 | 8/2005 | Perkins et al. | |
| 2006/0174364 A1* | 8/2006 | Christmann ....... | C12N 15/8509 800/19 |
| 2007/0004002 A1 | 1/2007 | Okazaki | |
| 2011/0318832 A1 | 12/2011 | Cech et al. | |
| 2012/0064578 A1 | 3/2012 | Perkins et al. | |
| 2012/0093785 A1 | 4/2012 | Oshimura et al. | |
| 2014/0295501 A1 | 10/2014 | Katona et al. | |
| 2015/0004703 A1* | 1/2015 | Mostoslavsky ....... | C12N 15/86 435/325 |
| 2018/0010150 A1 | 1/2018 | Perkins et al. | |

FOREIGN PATENT DOCUMENTS

| EP | 2218786 A4 | 6/2011 |
| EP | 2522725 B1 | 10/2016 |
| EP | 1559782 B1 | 12/2016 |
| WO | 9740183 A2 | 10/1997 |
| WO | 0018941 A1 | 4/2000 |
| WO | 02096923 B1 | 5/2004 |

OTHER PUBLICATIONS

Missirlis et al, A high-throughput screen identifying sequence and promiscuity characteristics of the loxP spacer region in Cre-mediated recombination, BMC Genomics 2006, pp. 1-13.*
Liskovykh M, et al. Stable maintenance of de novo assembled human artificial chromosomes in embryonic stem cells and their differentiated progeny in mice. Cell Cycle 2015, p. 1268-1273.*
Kriz et al, A plasmid-based multigene expression system for mammalian cells, Nature Communciations, 2010, pp. 1-6.*
Nandy et al, Gene stacking in plant cell using recombinases for gene integration and nucleases for marker gene deletion, BMC Biotechnology (2015), p. 1-12.*
Basu, J., "Artificial and Engineered Chromosomes: Non-Integrating Vectors for Gene Therapy." Trends in Molecular Medicine, Elsevier Current Trends, vol. 11 (5), pp. 251-258 (2005).
Ikeno, M et al., "Construction of YAC-based mammalian artificial chromosomes", Nature Biotechnology, (19980500), vol. 16, No. 5, pp. 431-439, XP009060040.
Katoh, et al., (2004) "Construction of a novel human artificial chromosome vector for gene delivery." Biochem. Biophys. Res. Comm. 321:280-290.
Kazuki, et al., "Refined human artificial chromosome vectors for gene therapy and animal transgenesis." Gene Therapy, vol. 18(4):384-393 (2010).
Kazuki, Y et al., "Human Artificial Chromosomes for Gene Delivery and the Development of Animal Models", Molecular Therapy, (2011) 19(9):1591-1601. doi:10.1038/mt.2011.136, XP055581607.
Kouprina et al., (2013) "A new generation of human artificial chromosomes for functional genomics and gene therapy", Cell Mol Life Sci., vol. 70, No. 7, pp. 1135-1148, XP055470579.
Kouprina, et al., (2014) "Human Artificial Chromosome-Based Gene Delivery Vectors for Biomedicine and Biotechnology." Expert Opinion on Drug Delivery. 11(4):517-535.
Kurosaki, et al., "Integration-free and stable expression of FVIII using a human artificial chromosome." Journal of Human Genetics, vol. 56 (10), pp. 727-733 (2011).
Lindenbaum et al., "A mammalian artificial chromosome engineering system (ACE System) applicable to biopharmaceutical protein production, transgenesis and gene-based cell therapy," Nucleic Acids Research, (2004), vol. 32, No. 21, pp. 1-15 (p. e172, XP002741726).

(Continued)

*Primary Examiner* — Maria Marvich
(74) *Attorney, Agent, or Firm* — Susan J. Myers Fitch

(57) ABSTRACT

The present invention provides a novel method for targeted integration of nucleic acids onto an autonomously replicating nucleic acid using site-directed recombination that allows for sequential loading of multiple delivery vectors using a single selectable marker.

21 Claims, 4 Drawing Sheets

Specification includes a Sequence Listing.

(56) References Cited

OTHER PUBLICATIONS

Martella, et al., "Mammalian Synthetic Biology: Time for Big MACs." ACS Synthetic Biology, vol. 5 (10), pp. 1040-1049 (2016).
Ren, X et al., "A Novel Human Artificial Chromosome Vector Provides Effective Cell Lineage-Specific Transgene Expression in Human Mesenchymal Stem Cells", Stem Cells, (Nov. 1, 2005), vol. 23, No. 10, doi:10.1634/stemcells.2005-0021, pp. 1608-1616, XP055473399.
Rocchi, et al., (2010) "*Escherichia coli*-Cloned CTFR Loci Relevant for Human Artificial Chromosome Therapy." Human Gene Therapy, 21:1077-1092.
Shitara, et al., 2008, "Telomerase-mediated life-span extension of human primary fibroblasts by human artificial chromosome (HAC) vector." Biochem. Biophys. Res. Commun. 369(3):807-11.
Suzuki, et al., (2014), "A Novel System for Simultaneous or Sequential Integration of Multiple Gene-Loading Vectors into a Defined Site of a Human Artificial Chromosome." Plos One. 9(10), pp. 1-9 (2014).
Takiguchi, et al., "A Novel and Stable Mouse Artificial Chromosome Vector." ACS Synthetic Biology, vol. 3 (12), pp. 903-914 (2014).
Toth, et al., "Novel Method to Load Multiple Genes onto a Mammalian Artificial Chromosome." Plos One, Public Library of Science, US, vol. 9 (1), pp. e85565-1 (2014).
Vanderbyl, S et al., "Transfer and Stable Transgene Expression of a Mammalian Artificial Chromosome into Bone Marrow-Derived Human Mesenchymal Stem Cells", Stem Cells, (20040500), vol. 22, No. 3, doi:doi:10.1634/stemcells.22-3-324, pp. 324-333, XP002506658.
Yamaguchi, et al., 2011 "A Method for Producing Transgenic Cells Using a Multi-Integrase System on a Human Artificial Chromosome Vector." PLoS ONE 6(2): e17267. https://doi.org/10.1371/journal.pone.0017267.
Brenda Grimes and Zoia Monaco, "Artificial and Engineered Chromosomes: Developments and Prospects for Gene Therapy," Chromosoma, (2005), 114:230-241.
Bruce Bunnell, et al., "Development of Mammalian Artificial Chromosomes for the Treatment of Genetic Diseases: Sandhoff and Krabbe Diseases," Expert Opin. Biol. Therapy (2005) 5(2):95-206.
Li Lin, et al., "Efficient linking and transfer of multiple genes by a multigene assembly and transformation vector system," PNAS, (2003), p. 5962-5967, vol. 100, No. 10.
Tomohiro Tsuduki, et al., "An Artificially Constructed De Novo Human Chromosome Behaves Almost Identically to its Natural Counterpart during Metaphase and Anaphase in Living Cells," Molecular and Cellular Biology (2006), vol. 26, No. 20, p. 7682-7695.
Yueju Wang, et al., "Recombinase Technology: Applications and Possibilities," Plant Cell Rep., (2011), 30:267-285.

\* cited by examiner

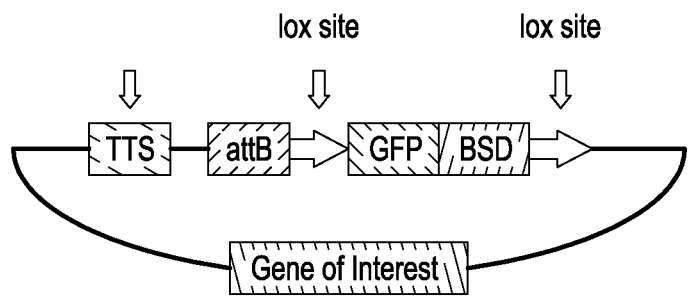

FIG. 1

```
┌─────────────────────────────────────────────────────┐
│ INTEGRATE A FIRST DELIVERY VECTOR COMPRISING A MARKER GENE │
│ AND A DRUG RESISTANT GENE AND A FIRST NUCLEIC ACID OF INTEREST │
│ ONTO AN AUTONOMOUSLY REPLICATING NUCLEIC ACID UTILIZING A │
│ FIRST RECOMBINATION SYSTEM │
└─────────────────────────────────────────────────────┘
                           │
                           ▼
┌─────────────────────────────────────────────────────┐
│ EXCISE THE MARKER GENE AND THE DRUG RESISTANT GENE UTILIZING │
│ A SECOND RECOMBINATION SYSTEM WITH SIGNAL SITES ALPHA, WHERE │
│ THE FIRST NUCLEIC ACID OF INTEREST REMAINS ON THE AUTONOMOUSLY │
│ REPLICATING NUCLEIC ACID │
└─────────────────────────────────────────────────────┘
                           │
                           ▼
┌─────────────────────────────────────────────────────┐
│ INTEGRATE A SECOND DELIVERY VECTOR COMPRISING THE SAME │
│ MARKER GENE AND THE SAME DRUG RESISTANT GENE AND A SECOND │
│ NUCLEIC ACID OF INTEREST ONTO THE AUTONOMOUSLY REPLICATING │
│ NUCLEIC ACID UTILIZING THE FIRST RECOMBINATION SYSTEM │
└─────────────────────────────────────────────────────┘
                           │
                           ▼
┌─────────────────────────────────────────────────────┐
│ EXICISE THE MARKER GENE AND THE DRUG RESISTANT GENE UTILIZING │
│ THE SECOND RECOMBINATION SYSTEM WITH SIGNAL SITES BETA, WHERE │
│ THE SECOND NUCLEIC ACID OF INTEREST REMAINS ON THE │
│ AUTONOMOUSLY REPLICATING NUCLEIC ACID │
└─────────────────────────────────────────────────────┘
```

FIG. 2

SEQUENTIAL LOADINGS OF MULTIPLE DELIVERY VECTORS USING A SINGLE SELECTABLE MARKER

CROSS REFERENCE TO RELATED APPLICATIONS

This International PCT Patent Application claims priority to U.S. Provisional Patent Application No. 62/321,711 filed Apr. 12, 2016.

STATEMENT REGARDING GOVERNMENT SUPPORT

This invention was made with Government support under contract D15PC00008 awarded by DARPA. The Government has certain rights in this invention.

FIELD OF THE INVENTION

The present invention encompasses methods for drug-free selection of targeted integrants delivered onto an autonomously replicating nucleic acid using site-directed recombination that allows for sequential loadings of multiple delivery vectors using a single selectable marker.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The ability to generate fully-functional mammalian synthetic chromosomes represents a powerful system for cell-based correction of genetic disorders, production of recombinant proteins in transgenic animals, analysis of regulation and expression of large human genes in a variety of cell types as well as in animal models of human disease, studies of meiosis and chromosome structure, directing cell differentiation and dedifferentiation, formation of induced pluripotent stem cells, creation of novel autocrine and paracrine cellular communication networks, creation of multi-expression systems capable of stoichiometric production of multiple encoded factors, production of biological circuits, insertion of DNA elements capable of probing the nuclear architecture and downstream uses for regulating genomic expression using discovered interactions in the nuclear architecture, and manipulation of large DNA elements such as but not limited to chromosome arm exchange onto the synthetic chromosome or incorporation of multiple large DNA elements onto the synthetic chromosome.

Fully-functional mammalian synthetic chromosomes offer several advantages over viral-based delivery systems including increased payload size, the fact that extrachromosomal maintenance avoids potential host-cell disruption, avoidance of transcriptional silencing of introduced genes and possible immunological complications, and mammalian synthetic chromosomes can be derived from and tailored to the species into which the synthetic chromosome is to be inserted. However, while successful production of mammalian synthetic chromosomes has been demonstrated—including mammalian synthetic chromosomes with multiple integration sites—currently the methods for loading multiple nucleic acids onto mammalian synthetic chromosomes are limited and there are no efficient methods that allow for an unlimited number of recyclings of the same marker genes and drug resistance genes. The ability to efficiently identify and isolate cells with properly integrated delivery vectors by flow cytometry will greatly improve bioengineering of synthetic chromosomes. Importantly, the elimination of the requirement of using drug selection alleviates a potential host response to expressed drug markers. The present invention provides methods that provide these advantages.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

The present invention encompasses methods for drug-free selection of targeted integrants delivered onto an autonomously replicating nucleic acid using site-directed recombination that allows for sequential loadings of multiple delivery vectors using a single selectable marker.

In some embodiments, the present invention provides a method for sequential loadings of multiple delivery vectors using a single selectable marker comprising: integrating a first delivery vector comprising a marker gene and a drug resistant gene and a first nucleic acids of interest onto an autonomously replicating nucleic acid using a first recombination system; excising the marker gene and the drug resistant gene from the autonomously replicating nucleic acid using a second recombination system with signal sites alpha, wherein the first nucleic acid of interest remains on the autonomously replicating nucleic acid; integrating a second delivery vector comprising the marker gene and the drug resistant gene and a second nucleic acid of interest onto the autonomously replicating nucleic acid using the first recombination system; and excising the marker gene and the drug resistant gene from the autonomously replicating nucleic acid using the second recombination system with signal sites beta, wherein the second nucleic acid of interest remains on the autonomously replicating nucleic acid.

In yet other embodiments, the present invention further comprises the steps of integrating a third delivery vector comprising the marker gene and the drug resistant gene and a third nucleic acid of interest onto the autonomously replicating nucleic acid utilizing the first recombination system; and excising the marker gene and the drug resistant gene utilizing the second recombination system with signal sites gamma, wherein the third nucleic acid of interest remains on the autonomously replicating nucleic acid. In preferred embodiments, the steps of the methods are repeated until a desired number of nucleic acids of interest are loaded onto the autonomously replicating nucleic acid.

In some aspects of these embodiments, the autonomously replicating nucleic acid is an endogenous chromosome, and in other aspects, the autonomously replicating nucleic acid is a synthetic chromosome. In some aspects, the synthetic chromosome is a mammalian chromosome, and in some aspects, the synthetic chromosome is a human synthetic chromosome.

In some aspects, the first recombination system is a Lambda integrase system, and in some aspects, the second recombination system is a Cre/lox recombination system. In some aspects, the signal sites alpha, beta, and gamma are selected from Lox2272, Lox5171, LoxM2, and LoxP, but all of signal sites alpha, beta, and gamma are different.

In some aspects, the marker gene is a gene coding for a fluorescent protein.

These and other aspects and uses of the invention will be described in the detailed description.

BRIEF DESCRIPTION OF THE FIGURES

FIG. 1 is a simplified graphic of a delivery vector according to the present invention.

FIG. 2 is a simplified flow chart of method steps for targeted integration of nucleic acids onto an autonomously replicating nucleic acid using site-directed recombination that allows for sequential loading of multiple delivery vectors using a single selectable marker.

DETAILED DESCRIPTION OF THE INVENTION

Figure 3:
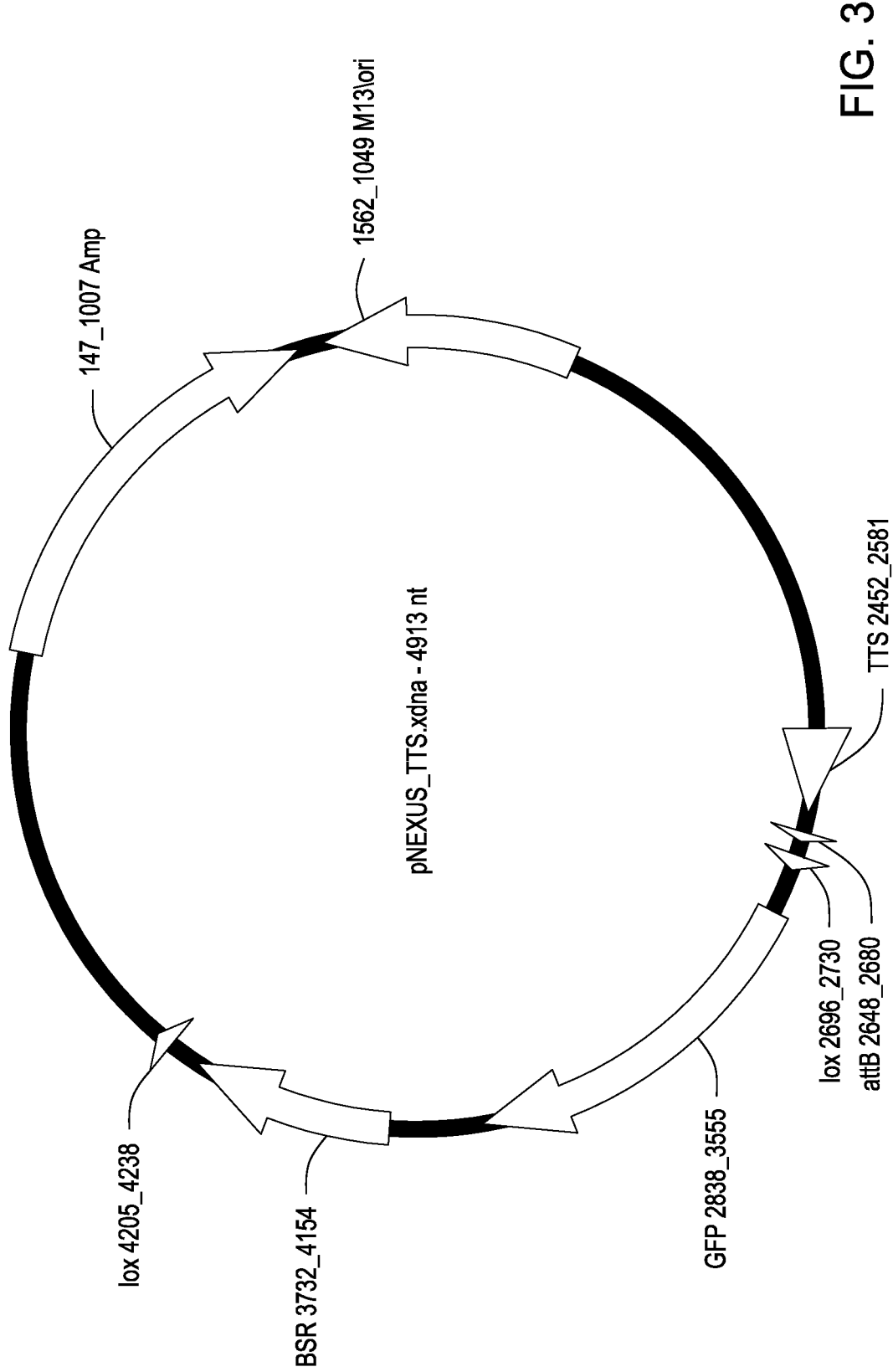
FIG. 3 is a map of the pNEXUS_TTS loading vector, with a promoterless GFP::BSD fusion gene flanked by lox sites.

The methods described herein may employ, unless otherwise indicated, conventional techniques and descriptions of molecular biology (including recombinant techniques), cell biology, biochemistry, and cellular engineering technology, all of which are within the skill of those who practice in the art. Such conventional techniques include oligonucleotide synthesis, hybridization and ligation of oligonucleotides, transformation and transduction of cells, engineering of recombination systems, creation of transgenic animals and plants, and human gene therapy. Specific illustrations of suitable techniques can be had by reference to the examples herein. However, equivalent conventional procedures can, of course, also be used. Such conventional techniques and descriptions can be found in standard laboratory manuals such as *Genome Analysis: A Laboratory Manual Series* (Vols. I-IV) (Green, et al., eds., 1999); *Genetic Variation: A Laboratory Manual* (Weiner, et al., eds., 2007); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); *Protein Methods* (Bollag et al., John Wiley & Sons 1996); *Nonviral Vectors for Gene Therapy* (Wagner et al. eds., Academic Press 1999); *Viral Vectors* (Kaplift & Loewy, eds., Academic Press 1995); *Immunology Methods Manual* (Lefkovits ed., Academic Press 1997); *Gene Therapy Techniques, Applications and Regulations From Laboratory to Clinic* (Meager, ed., John Wiley & Sons 1999); M. Giacca, *Gene Therapy* (Springer 2010); *Gene Therapy Protocols* (LeDoux, ed., Springer 2008); *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011); *Stem Cell Therapies: Opportunities for Ensuring the Quality and Safety of Clinical Offerings: Summary of a Joint Workshop* (Board on Health Sciences Policy, National Academies Press 2014); *Essentials of Stem Cell Biology*, Third Ed., (Lanza and Atala, eds., Academic Press 2013); and *Handbook of Stem Cells*, (Atala and Lanza, eds., Academic Press 2012), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by the appended claims.

Note that as used in the present specification and in the appended claims, the singular forms "a," "and," and "the" include plural referents unless the context clearly dictates otherwise. Thus, for example, reference to "a composition" refers to one or mixtures of compositions, and reference to "an assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value between the upper and lower limit of that range and any other stated or intervening value in that stated range is encompassed within the invention. The upper and lower limits of these smaller ranges may independently be included in the smaller ranges, subject to any specifically excluded limit in the stated range. Where the stated range includes both of the limits, ranges excluding only one of those included limits are also included in the invention.

In the following description, numerous specific details are set forth to provide a more thorough understanding of the present invention. However, it will be apparent to one of ordinary skill in the art upon reading the specification that the present invention may be practiced without one or more of these specific details. In other instances, well-known features and procedures well known to those skilled in the art have not been described in order to avoid obscuring the invention.

Definitions

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

An "autonomously replicating nucleic acid" comprises any autonomously-replicating nucleic acid within a cell, including synthetic chromosomes and endogenous chromosomes.

"Binding" as used herein (e.g., with reference to an nucleic acid-binding domain of a polypeptide) refers to a non-covalent interaction between a polypeptide and a nucleic acid. While in a state of non-covalent interaction, the polypeptide and nucleic acid are said to be "associated", "interacting", or "binding". Binding interactions are generally characterized by a dissociation constant (Kd) of less than $10^{-6}$ M to less than $10^{-15}$ M. "Affinity" refers to the strength of binding, increased binding affinity being correlated with a lower Kd.

By "binding domain" it is meant a polypeptide or protein domain that is able to bind non-covalently to another molecule. A binding domain can bind to, for example, a DNA molecule (a DNA-binding protein), an RNA molecule (an RNA-binding protein) and/or a protein molecule (a protein-binding protein).

A "centromere" is any nucleic acid sequence that confers an ability of a chromosome to segregate to daughter cells through cell division. A centromere may confer stable segregation of a nucleic acid sequence, including a synthetic chromosome containing the centromere, through mitotic and meiotic divisions. A centromere does not necessarily need to be derived from the same species as the cells into which it is introduced, but preferably the centromere has the ability to promote DNA segregation in cells of that species. A "dicentric" chromosome is a chromosome that contains two centromeres. A "formerly dicentric chromosome" is a chromosome that is produced when a dicentric chromosome fragments. A "chromosome" is a nucleic acid molecule—and associated proteins—that is capable of replication and segregation in a cell upon division of the cell. Typically, a chromosome contains a centromeric region, replication origins, telomeric regions and a region of nucleic acid between the centromeric and telomeric regions. An "acrocentric chromosome" refers to a chromosome with arms of unequal length.

A "coding sequence" or a sequence that "encodes" a peptide is a nucleic acid molecule that is transcribed (in the case of DNA) and translated (in the case of mRNA) into a polypeptide in vivo when placed under the control of appropriate control sequences. The boundaries of the coding sequence typically are determined by a start codon at the 5' (amino) terminus and a translation stop codon at the 3' (carboxy) terminus.

The term DNA "control sequences" refers collectively to promoter sequences, polyadenylation signals, transcription termination sequences (TTS), upstream regulatory domains, origins of replication, internal ribosome entry sites, enhancers, and the like, which collectively provide for the replication, transcription and translation of a coding sequence in a recipient cell. Not all of these types of control sequences need to be present so long as a selected coding sequence is capable of being replicated, transcribed and translated in an appropriate host cell.

"Endogenous chromosomes" refer to chromosomes found in a cell prior to generation or introduction of a synthetic chromosome.

As used herein, "euchromatin" refers to chromatin that stains diffusely and that typically contains genes, and "heterochromatin" refers to chromatin that remains unusually condensed and is thought to be transcriptionally inactive. Highly repetitive DNA sequences (satellite DNA) are usually located in regions of the heterochromatin surrounding the centromere.

The terms "heterologous DNA" or "foreign DNA" (or "heterologous RNA" or "foreign RNA") are used interchangeably and refer to DNA or RNA that does not occur naturally as part of the genome in which it is present, or is found in a location or locations and/or in amounts in a genome or cell that differ from that in which it occurs in nature. Examples of heterologous DNA include, but are not limited to, DNA that encodes a gene product or gene product(s) of interest. Other examples of heterologous DNA include, but are not limited to, DNA that encodes traceable marker proteins as well as regulatory DNA sequences.

"Operably linked" refers to an arrangement of elements where the components so described are configured so as to perform their usual function. Thus, control sequences operably linked to a coding sequence are capable of effecting the expression of the coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome), and may still have interactions resulting in altered regulation.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase I, II or III. Promoters of use in the invention can be constitutive or inducible.

"Recognition sequences" are particular sequences of nucleotides that a protein, DNA, or RNA molecule, or combinations thereof (such as, but not limited to, a restriction endonuclease, a modification methylase or a recombinase) recognizes and binds. For example, a recognition sequence for Cre recombinase is a 34 base pair sequence containing two 13 base pair inverted repeats (serving as the recombinase binding sites) flanking an 8 base pair core and designated loxP (see, e.g., Sauer, Current Opinion in Biotechnology, 5:521-527 (1994)). Other examples of recognition sequences, include, but are not limited to, attB and attP, attR and attL and others that are recognized by the recombinase enzyme bacteriophage Lambda Integrase. The recombination site designated attB is an approximately 33 base pair sequence containing two 9 base pair core-type Int binding sites and a 7 base pair overlap region; attP is an approximately 240 base pair sequence containing core-type Int binding sites and arm-type Int binding sites as well as sites for auxiliary proteins IHF, FIS, and Xis (see, e.g., Landy, Current Opinion in Biotechnology, 3:699-7071 (1993)).

A "recombinase" is an enzyme that catalyzes the exchange of DNA segments at specific recombination sites. An integrase refers to a recombinase that is usually derived from viruses or transposons, as well as perhaps ancient viruses. "Recombination proteins" include excisive proteins, integrative proteins, enzymes, co-factors and associated proteins that are involved in recombination reactions using one or more recombination sites (see, Landy, Current Opinion in Biotechnology, 3:699-707 (1993)). The recombination proteins used in the methods herein can be delivered to a cell via an expression cassette on an appropriate vector, such as a plasmid, and the like. In other embodiments, recombination proteins can be delivered to a cell in protein form in the same reaction mixture used to deliver the desired nucleic acid(s). In yet other embodiments, the recombinase could also be encoded in the cell and expressed upon demand using a tightly controlled inducible promoter.

"Ribosomal RNA" (rRNA) is the specialized RNA that forms part of the structure of a ribosome and participates in the synthesis of proteins. Ribosomal RNA is produced by transcription of genes which, in eukaryotic cells, are present in multiple copies. In human cells, the approximately 250 copies of rRNA genes (i.e., genes which encode rRNA) per haploid genome are spread out in clusters on at least five different chromosomes (chromosomes 13, 14, 15, 21 and 22). In human cells, multiple copies of the highly conserved rRNA genes are located in a tandemly arranged series of rDNA units, which are generally about 40-45 kb in length and contain a transcribed region and a nontranscribed region known as spacer (i.e., intergenic spacer) DNA which can vary in length and sequence.

As used herein the term "selectable marker" refers to a gene introduced into a cell, particularly in the context of this invention into cells in culture, that confers a trait suitable for artificial selection. General use selectable markers are well-known to those of ordinary skill in the art. In preferred embodiments, selectable markers for use in a human synthetic chromosome system should be non-immunogenic in the human and include, but are not limited to: human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34$^+$ cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2a; detectable by Mab-FITC); Methylguanine-DNA methyltransferase (MGMT; selectable by carmustine); and Cytidine deaminase (CD; selectable by Ara-C). Drug selectable (drug resistant or drug resistance) markers such as puromycin, hygromycin, blasticidin, G418, tetracycline may also be employed. In addition, using FACs sorting, any fluorescent marker gene may be used for positive selection, as may chemiluminescent markers (e.g. Halotags), and the like.

"Site-specific recombination" refers to site-specific recombination that is effected between two specific sites on a single nucleic acid molecule or between two different molecules that requires the presence of an exogenous protein, such as an integrase or recombinase. Certain site-specific recombination systems can be used to specifically delete, invert, or insert DNA, with the precise event controlled by the orientation of the specific sites, the specific system and the presence of accessory proteins or factors. In addition, segments of DNA can be exchanged between chromosomes (chromosome arm exchange).

"Synthetic chromosomes" (also referred to as "artificial chromosomes") are nucleic acid molecules, typically DNA, that stably replicate and segregate alongside endogenous chromosomes in cells that have the capacity to accommodate and express heterologous genes. A "mammalian synthetic chromosome" refers to chromosomes that have an active mammalian centromere(s). A "human synthetic chromosome" refers to a chromosome that includes a centromere that functions in human cells and that preferably is produced in human cells. For exemplary artificial chromosomes, see, e.g., U.S. Pat. Nos. 8,389,802; 7,521,240; 6,025,155; 6,077, 697; 5,891,691; 5,869,294; 5,721,118; 5,712,134; 5,695, 967; and 5,288,625 and published International PCT application Nos. WO 97/40183 and WO 98/08964.

The terms "subject", "individual" or "patient" may be used interchangeably herein and refer to a mammal, and in some embodiments, a human.

A "vector" is a replicon, such as plasmid, phage, viral construct, cosmid, bacterial artificial chromosome, P-1 derived artificial chromosome or yeast artificial chromosome to which another DNA segment may be attached. In some instances a vector may be a chromosome such as in the case of an arm exchange from one endogenous chromosome engineered to comprise a recombination site to a synthetic chromosome. Vectors are used to transduce and express a DNA segment in cell.

The Invention

The present invention provides methods for drug-free selection of targeted integrants delivered onto an autonomously replicating nucleic acid using site-directed recombination that allows for sequential loadings of multiple delivery vectors employing a single selectable marker.

The present invention provides a novel method of selecting for site-directed insertion of a nucleic acid delivery vector onto an autonomously replicating nucleic acid such as a synthetic chromosome containing a desired target site. As an example, a delivery vector that contains the bacteriophage lambda target site attB that is linked upstream of a fluorescent protein gene (green fluorescent protein) in frame with a drug resistant gene (blasticidin resistance) such that both the fluorescent protein gene and the drug resistant gene form a protein with both functional fluorescence and drug resistance is provided. The fluorescent protein gene and drug resistance gene sequences are flanked by a set of a site-specific recombination sequences from a second recombination system, such as lox sites from the Cre/lox recombination system. Furthermore, the delivery vector contains a strong transcriptional stop upstream of the attB sequence and the nucleic acid of interest to be targeted onto the autonomously replicating nucleic acid (see FIG. 1; TTS). Incorporation of TTS upstream of the attB recombination site prevents permiscuous transcription from upstream delivery vector sequences (i.e. false positive integrants), thereby allowing for efficient identification of properly integrated delivery vectors onto the synthetic platform chromosome. In this example, the target nucleic acid contains one or more attP bacteriophage lambda DNA sequence elements. The target nucleic acid may be an endogenous chromosome, a synthetic chromosome or any autonomously replicating nucleic acid housed within a cell.

FIG. 2 is a simplified flow chart of method steps for targeted integration of nucleic acids onto an autonomously replicating nucleic acid using site-directed recombination that allows for sequential loading of multiple delivery vectors using a single selectable marker. In step 1 of FIG. 2, a first delivery vector comprising a marker gene and a drug resistant gene and a first nucleic acid of interest is integrated onto an autonomously replicating nucleic acid via a first recombination system. In step 2, the marker gene and the drug resistant gene are excised from the autonomously replicating nucleic acid via a second recombination system with signal sites alpha, where the first nucleic acid of interest remains on the autonomously replicating nucleic acid. In step 3, a second delivery vector comprising the same marker gene and same drug resistant gene and a second nucleic acid of interest is integrated onto an autonomously replicating nucleic acid utilizing the first recombination system, and in step 4, the marker gene and the drug resistant gene are once again excised utilizing the second recombination system with signal sites beta, where the second nucleic acid of interest remains on the autonomously replicating nucleic acid. These steps can be repeated until all nucleic acids of interest have been loaded onto the autonomously replicating nucleic acid.

Using standard nucleic acid delivery methods or, when necessary, specialized nucleic acid delivery methods for the cell type of interest carrying the target nucleic acid (e.g., attP), the delivery vector such as that described, above, and illustrated in FIG. 1 is delivered to the cell of interest. Simultaneously or sequentially with the delivery vector, a recombinase is also delivered to the cell of interest. The recombinase may be in the form of 1) a vector encoding the recombinase, 2) a purified recombinase protein or 3) an encapsulated recombinase protein. Following delivery of the delivery vector and recombinase, the cells are cultured for approximately three days then harvested by standard methodology for Fluorescence Activated Cell sorting (FACs). In one example, cells expressing the green fluorescent protein are single-cell sorted into individual wells of a 96-well cell culture plate containing appropriate cell culture medium for the cell type (i.e., selected cell clones comprising the autonomously replicating nucleic acid). The sorted cells are maintained in culture for 1-3 weeks to allow expansion of the individual clones to a cell number adequate for harvesting for cold storage and molecular analysis while continuing the culture for assessment of the expression or function of the nucleic acid of interest. Analysis includes but is not limited to 1) polymerase chain reaction (PCR) analysis with appropriate primer sets used to assess whether the delivery vector was correctly integrated at the target site; 2) assessment of activity of the nucleic acid of interest, including but not limited to a metabolic test; measurement of transcript level, a phenotypic assay, or detection of the protein product using an antibody specific to the protein product of the gene of interest; and/or 3) DNA sequencing of the integrated delivery vector.

Sequential loading of multiple delivery vectors onto the autonomously replicating nucleic acid is accomplished by removal and reuse of the fluorescent protein gene and drug resistance gene. The removal of these DNA sequences is performed by a second recombination system (e.g., Cre/lox in this example). To remove the fluorescent protein gene and drug resistance gene, the cell line carrying the first nucleic acid sequence of interest is exposed to the Cre recombinase which directs the recombination and excision of the direct repeats of the lox sequences flanking the fluorescent protein gene and drug resistance gene (or inversion of the same leaving them without a promoter if the lox sequences are situated as inverted repeats flanking the fluorescent protein gene and drug resistance gene). The exposure to the second recombinase may be accomplished by introduction of a nucleic acid vector encoding the second recombinase, the purified recombinase protein or an encapsulated recombinase using standard methodologies. Following introduction of the recombinase, the cells are cultured for approximately three days, then harvested for FACs sorting whereby those cells that are no longer expressing the fluorescent protein are single cell sorted into individual wells of a 96-well cell culture plate containing appropriate cell culture medium for the cell type (i.e., selected cell comprising the autonomously replicating nucleic acid). The sorted cells are maintained in culture for 1-3 weeks to allow expansion of the individual clones to a cell number adequate for harvesting for cold storage and molecular analysis while continuing the culture for reassessment of the expression or function of the first nucleic acid of interest.

Following confirmation of the proper excision of the fluorescent protein gene and drug resistance gene, introduction of a second gene of interest may be accomplished in the same manner as was used for the first gene of interest. In this process, the second delivery vector carrying a second nucleic acid sequence of interest has the same fluorescent protein gene and same drug resistance gene flanked by an alternate lox sequence (e.g., loxP 511) and is introduced to the cells comprising the autonomously replicating nucleic acids. The alteration in the, e.g., lox sequence in subsequent delivery vectors is critical to eliminate the potential of Cre/lox recombination occurring between residual lox sites that reside on the autonomously replicating nucleic acid following excision of the fluorescent protein gene and drug resistance gene and the lox sites on the newly-integrated delivery vector. For example, exemplary lox variant sequences are shown in Table 1:

TABLE 1

| Lox Variant | Spacer sequence |
| --- | --- |
| Lox2272 | AAGTATCC |
| Lox5171 | ATGTGTAC |
| LoxM2 | AGAAACCA |
| LoxP | ATGTATGC |

Analysis for proper excision includes but is not limited to 1) polymerase chain reaction (PCR) analysis with appropriate primer sets used to assess whether the delivery vector was correctly integrated at the target site; 2) assessment of activity of the nucleic acid of interest, including but not limited to a metabolic test; measurement of transcript level, a phenotypic assay, or detection of the protein product using an antibody specific to the protein product of the gene of interest; and/or 3) DNA sequencing of the integrated delivery vector. As before, the removal of the fluorescent protein gene and drug resistance gene is performed by a second recombination system.

The methods of the present invention allow for an unlimited number of recyclings of the fluorescent protein gene and drug resistance gene. The method also can be used to incorporate multiple recombination systems in addition to multiple recombination sites of a single recombination system.

Notably, the methods of the present invention alleviate the need for drug selection during the delivery of the nucleic acid to the autonomous replicating nucleic acid. In turn, the elimination of the requirement for drug selection potentially alleviates host immune responses to expressed drug markers. Furthermore, use of multiple fluorescent markers (markers of different fluorescent wavelengths) permits the co-delivery of multiple nucleic acids onto the autonomous replicating piece of DNA.

Delivery Vectors

The choice of the delivery vector to be used in delivery of the marker gene, drug resistant gene and nucleic acids of interest to the autonomously replicating nucleic acids depends upon a variety of factors such as the type of cell in which propagation is desired. The choice of appropriate vector is well within the skill of those in the art, and many vectors are available commercially. To prepare the constructs, a polynucleotide comprising the marker gene, drug resistant gene and an nucleic acid of interest (see FIG. 1) is inserted into a vector, typically by means of ligation of a sequence into a cleaved restriction enzyme site in the vector. Alternatively, the desired nucleotide sequence can be inserted by homologous recombination or site-specific recombination. Nucleic acids containing such sequences can be added by, for example, ligation of oligonucleotides, or by polymerase chain reaction using primers comprising both the region of homology and a portion of the desired nucleotide sequence. Exemplary vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Additional vectors include bacterial artificial chromsomes (BACs), those based on a functional fertility plasmid (F-plasmid), yeast artificial chromosomes (YACs), and P1-derived artificial chromsomes, DNA constructs derived from the DNA of P1 bacteriophage (PACS). Alternatively and preferably, recombinant virus vectors may be engineered, including but not limited to those derived from viruses such as herpes virus, retroviruses, vaccinia virus, poxviruses, adenoviruses, lentiviruses, adeno-associated viruses or bovine papilloma virus.

Delivery of the Delivery Vectors into Cells

The vectors chosen to deliver the marker gene, drug resistant gene and nucleic acids of interest to the autonomously replicating nucleic acids can be delivered to the cells containing the autonomously replicating nucleic acid by any method known in the art. The terms transfection and transformation refer to the taking up of exogenous nucleic acid, e.g., an expression vector, by a host cell whether or not any coding sequences are, in fact, expressed. Numerous methods of transfection are known to the ordinarily skilled artisan, for example, by *Agrobacterium*-mediated transformation, protoplast transformation (including polyethylene glycol (PEG)-mediated transformation, electroporation, protoplast fusion, and microcell fusion), lipid-mediated delivery, liposomes, electroporation, sonoporation, microinjection, particle bombardment and silicon carbide whisker-mediated transformation and combinations thereof (see, e.g., Paszkowski, et al., EMBO J., 3:2717-2722 (1984); Potrykus, et al., Mol. Gen. Genet., 199:169-177 (1985); Reich, et al., Biotechnology, 4:1001-1004 (1986); Klein, et al., Nature, 327:70-73 (1987); U.S. Pat. No. 6,143,949; Paszkowski, et al., in *Cell Culture and Somatic Cell Genetics of Plants*, Vol. 6, Molecular Biology of Plant Nuclear Genes, (Schell and Vasil, eds., Academic Publishers 1989); and Frame, et al., Plant J., 6:941-948 (1994)); direct uptake using calcium phosphate (Wigler, et al., Proc. Natl. Acad. Sci. U.S.A., 76:1373-1376 (1979)); polyethylene glycol (PEG)-mediated DNA uptake; lipofection (see, e.g., Strauss, Meth. Mol. Biol., 54:307-327 (1996)); microcell fusion (Lambert, Proc. Natl. Acad. Sci. U.S.A., 88:5907-5911 (1991); U.S. Pat. No. 5,396,767; Sawford, et al., Somatic Cell Mol. Genet., 13:279-284 (1987); Dhar, et al., Somatic Cell Mol. Genet., 10:547-559 (1984); and McNeill-Killary, et al., Meth. Enzymol., 254:133-152 (1995)); lipid-mediated carrier systems (see, e.g., Teifel, et al., Biotechniques, 19:79-80 (1995); Albrecht, et al., Ann. Hematol., 72:73-79 (1996); Holmen, et al., In Vitro Cell Dev. Biol. Anim., 31:347-351 (1995); Remy, et al., Bioconjug. Chem., 5:647-654 (1994); Le Bolch, et al., Tetrahedron Lett., 36:6681-6684 (1995); and Loeffler, et al., Meth. Enzymol., 217:599-618 (1993)); or other suitable methods. Methods for delivery of synthetic chromosomes also are described in U.S. application Ser. No. 09/815,979. Successful transfection is generally recognized by detection of the presence of the heterologous nucleic acid within the transfected cell, such as, for example, any visualization of the heterologous nucleic acid, expression of a selectable marker or any indication of the operation of a vector within the host cell. For a description of delivery methods useful in practicing the present invention, see U.S. Pat. Nos. 5,011,776; 5,747,308; 4,966,843; 5,627,059; 5,681,713; Kim and Eberwine, Anal. Bioanal. Chem. 397 (8): 3173-3178 (2010).

Marker Genes

As discussed, above, the present invention utilizes marker genes that allow one to monitor delivery of the nucleic acids of interest to the autonomously replicating nucleic acid. The marker genes in preferred embodiments are proteins, such as a fluorescent, phosphorescent or chemiluminescent proteins. In preferred embodiments, the labels are fluorescent labels that are transcribed and translated by the target cells comprising the autonomously replicating nucleic acids into a protein. Fluorescent proteins of particular use in the invention include but are not limited to TagBFP, TagCFP, TagGFP2, TagYFP, TagRFP, FusionRed, mKate2, TurboGFP, TurboYFP, TurboRFP, TurboFP602, TurboFP635, or TurboFP650 (all available from Evrogen, Moscow); AmCyan1, AcvGFP1, ZsGreen1, ZsYellow1, mBanana, mOrange, mOrange2, DsRed-Express2, EsRed-Express, tdTomato, DsRed-Monomer, DsRed2, AsRed2, mStrawberry, mCherry, HcRed1, mRaspberry, E2-Crimson, mPlum, Dendra 2, Timer, and PAmCherry (all available from Clontech, Palo Alto, CA); HALO-tags; infrared (far red shifted) tags (available from Promega, Madison, WI); and other fluorescent tags known in the art, as well as fluorescent tags subsequently discovered.

Visualization and Monitoring

Localization of the translated fluorescent, phosphorescent or chemiluminescent proteins from the vector integrated into the autonomously replicating nucleic acid may be accomplished with fluorescent microscopy. Generally, the cells are excited with a light source at the excitation wavelength of the particular fluorescent labels being used and the resulting fluorescence at the emission wavelength is detected. In a preferred embodiment, the excitation light source is a laser appropriate for the excitation of the fluorescent label. A confocal microscope used to detect the labels may be automated with a computer-controlled stage to automatically scan the entire cell culture dish. Similarly, the microscope may be equipped with a phototransducer (e.g., a photomultiplier, a solid state array, a CCD camera, etc.) attached to an automated data acquisition system to automatically record the fluorescence signal produced by each cell or cell colony in culture. Alternatively, one may also employ flow cytometers that snap a photo of each "cell" as it passes by a laser (e.g. Flowsight (Amnis; Seattle, WA)); thus automating the assessment of each cell colony for production of a synthetic chromosome.

EXAMPLES

Example 1: De Novo Generation of Satellite DNA-Based Artificial Chromosome

For de novo production of synthetic chromomsomes, exogenous DNA sequences were introduced into HT1080 synthetic chromosome production cell line, and, upon integration into the pericentric heterochromatic regions of acrocentric chromosomes, a large-scale amplification of the short arms of the acrocentric chromosome (rDNA/centromere region) was triggered. During the amplification event, the centromere was duplicated resulting in a dicentric chromosome with two active centromeres. Subsequent mitotic events resulted in cleavage and resolution of the dicentric chromosome, leading to a breakoff of approximately 20-120 Mb in size comprised predominantly of satellite repeat sequences with subdomains of coamplified transfected transgene that may also contain amplified copies of rDNA. The newly-generated synthetic chromosome is validated by observation of fluorescent chromosome painting or FISH, via an endogenous chromosome tag and a synthetic chromosome tag that was engineered into the HT1080 synthetic chromosome production cell line.

The day before transfection, the HT1080 synthetic chromosome production cell line cells were split to a density of approximately 2.0 to $8.0 \times 10^4$ adherent cells into 24-well tissue culture dishes, and the vectors comprising the exogenous DNA were purified (e.g., using a Qiagen EndoFree Plasmid Maxi Kit), linearized, and the concentration of the vectors was determined for transfection. The cultured HT1080 cells were fed 3-5 hours before transfection. 225 ng of pSTV28HurDNA vector and 12.5 ng p15A7248lac-EFlattPPuro vector per 24-well semiconfluent tissue culture dish were used to transfect the HT1080 cells using standard transfection reagents, e.g., ThermoFisher Lipofectamine LTX, Promega's Viafect, or Invitrogen's Calcium Phosphate Transfection Kit. The pSTV28HurDNA vector comprises the ribosomal DNA sequences. The p15A7248lac- EFlattP-Puro vector comprises the components for the site-specific recombination system, the LacO repeats and an ampicillin and a puromycin resistance gene. Cells were maintained for 1-3 days post-transfection at which point they were trypsinized and replated onto a 10 cm dish. Selective medium was added to the 10 cm dish at the time of plating or 1-3 days post plating. Selective conditions were maintained for 10-21 days with media changed every 2-3 days. Antibiotic resistant clones were picked when a colony reached 2-3 mm in diameter. Colonies that were well separated were preferred. Cells were removed by use of a cloning cylinder and trypsin, and transferred to a 24-well plate for expansion.

Figure 4:
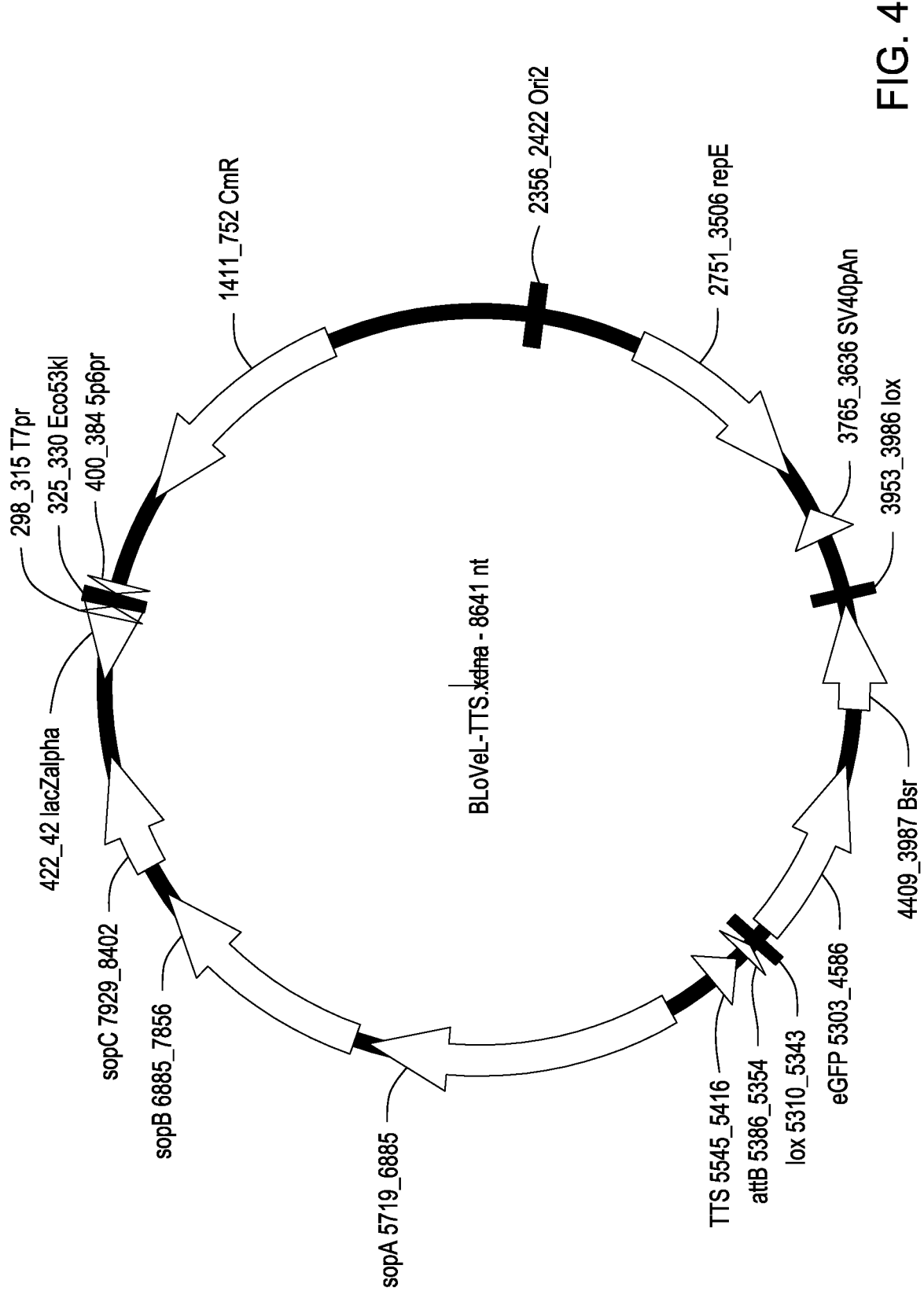
FIG. 4 is a map of the BLoVeL_TTS loading vector, with a promoterless eGFP::BSR fusion gene flanked by lox sites.

Example 2: Sequential Loading of Nucleic Acids of Interest onto the Synthetic Chromosome The Nexus-TSS (FIG. 3) (in pNEXus_TTX, the following elements are present: TTS=transcription termination signal; attB=site specific recombination site; lox=site specific recombination site; GFP=fluorescent protein; BSR= blasticidin resistance gene; M13Ori=origin of replication; Amp=ampicillin resistance gene), or BLoVeL-TTS (FIG. 4) (in BLoVeL-TSS, the following elements are present: sopA, sopB, and sopC=plasmid partitioning proteins; SV40pAn= SV40 poly A; TTS=transcription termination signal; attB=site specific recombination site; lox=site specific recombination site; eGFP=fluorescent protein; Bsr= blasticidin resistance gene; repE=replication initiation site; Ori2=origin of replication; CmR=chloramphenicol resistance gene; SV40polyAn=poly A; T7Pr=promoter; Eco53kI=restriction site vectors are used as the loading vector to sequentially insert nucleic acids of interest onto the synthetic chromosome. On day 0, the recipient cell line (e.g., HT1080) containing the synthetic chromosome (hSynC) is seeded at ~4E4 cells/well of a 24-well dish, such that the wells are ~70% confluent on Day 1. The cells are incubated overnight at 37° C., 5% $CO_2$, in appropriate medium (e.g., DMEM+10% FC3 for HT1080). On day 1, following the manufacturer's instructions (Fisher Scientific, Lipofectamine LTX with Plus reagent) both the delivery vector (e.g., Nexus-TSS, or BLoVeL-TSS) and the plasmid encoding the recombination protein (e.g. pCXLamIntR) are transfected into the HT1080 cells. Transfections are performed in duplicate so that a comparison of drug selection and direct cell sorting can be made. The Lipofectamine LTX is diluted in Opti-MEM medium (Gibco; 1.5 ul LTX/50 ul Opti-MEM for each well of the 24-well dish to be transfected), and 250 ng DNA is added to 50 ul diluted LTX in Opti-MEM (e.g. 125 ng BLoVeL-TSS plasmid and 125 ng pCXLamIntR per well). 0.25 ul PLUS reagent is added to each ~50 ul DNA-LTX-Opti_MEM sample, and each sample is incubated at room temperature for 5 minutes. The medium is then removed from the cells plated on Day 0 and fresh medium is used to replace the medium during the 5 minute incubation. DNA-lipid complexes are added to the cells and incubated at 37° C., 5% $CO_2$, in appropriate medium.

On days 2-24, drug selection is performed. The cells from one of the duplicate 24-well wells are trypsinized and transferred to a 10 cm dish with fresh medium containing drug selection (e.g., puromycin at 3 ug/ml). The cells are then incubated at 37° C., 5% $CO_2$, in appropriate medium, and monitored for colony formation. The medium is replaced approximately every 72 hours. When distinct colonies are formed (approximately 10 days), each colony is isolated by a glass cylinder, trypsinized and transferred to a well of a 24-well dish. These "clones" are then expanded in culture until sufficient cells are available to place the clone in cold storage and isolate genomic DNA (approximately 2 weeks; Promega Wizard SV Genomic DNA Purification) for PCR analysis.

Alternatively, the cells in the duplicate wells can be trypsinized and placed in a 6 cm dish with fresh medium lacking drug selection, and incubated at 37° C., 5% $CO_2$, in appropriate medium. On day 3 or 4 the cells in the 6 cm dish are trypsinized and applied to a cell sorter to single cell sort fluorescent cells that have integrated the vector and are expressing the fluorescent protein on the delivery vector (Nexus-TSS, or BLoVeL-TSS). Integration of the vector containing the gene/DNA elements of interest is identified by the production of a unique PCR product that spans the recombination site between the synthetic chromosome and the delivery vector (Nexus-TSS, or BLoVeL-TSS) using appropriate PCR primers. Negative control PCR reactions of water and host genomic DNA (e.g. HT1080) are performed in conjunction with the test genomic DNA samples. The PCR primers used to amplify the junction PCR products from BLoVeL-TSS vector integration are: Junction 1—Expected product size 392 bp (ACCGAGCTGC-AAGAACTCTTCCTC [SEQ ID No. 1] and ctcgccg-cagccgtgtaa [SEQ ID No. 2]); Junction 2—Expected product size 401 bp (gcgctaatgctctgttacaggt [SEQ ID No. 3] and GGAAAGCTGCCAGTGCCTTG [SEQ ID No. 4]). Note that the sorter identifies the in-frame GFP positive recombinants after integration, which is one of the unique aspects of the methods of the invention.

Upon identification of candidate clones with correct junction PCR product sizes, further PCR reactions are performed to confirm presence of the DNA elements of interest originally loaded onto the delivery vector and now residing on the synthetic chromosome (e.g. nucleic acids of interest 1, 2, 3 and so on).

Example 3: Excision of the GFP-BSD Cassette

The cell line with the synthetic chromosome is transfected with a CRE-expressing plasmid. On day 0, cells are seeded at 2E5 cells per 6 cm cell culture dish and incubated at 37° C. with 5% $CO_2$ overnight. On day 1, the CRE-expressing plasmid (e.g. PSF-CMV-CRE-CRE Recombinase Expression Vector; Sigma Aldrich) is transfected into the cell line with the synthetic chromosome with Lipofectamine LTX, following the manufacturer's protocol. The Lipofectamine LTX is diluted in Opti-MEM medium (Gibco; 7.25 ul LTX/500 ul Opti-MEM for each 6-well dish to be transfected), and 1.25 ug DNA is added to 500 ul diluted LTX in Opti-MEM (e.g. PSF-CMV-CRE-CRE Recombinase Expression Vector per 6 cm dish). 1.25 ul PLUS reagent is then added to each ~500 ul DNA-LTX-Opti_MEM sample, and incubated at room temperature 5 minutes. The medium is then removed from the cells plated on Day 0 and replaced with fresh medium during the 5 minute incubation. DNA-lipid complexes are added to the cells and incubated at 37° C., 5% $CO_2$, in appropriate medium. On day 2, the CRE transfected cells from the 6 cm dish are harvested by trypsinization and gated to collect non-fluorescent cells. The non-fluorescent cells have undergone CRE-lox recombination resulting in a removal of the eGFP-BSR cassette. The non-fluorescent cells can be single cell sorted into a 96-well dish and/or bulk sorted into a tube then plated to a cell culture dish (e.g. 6 cm dish). Cells are then monitored for fluorescence as they expand in culture. Those single cell clones showing no fluorescence are expanded in culture for cold storage and genomic DNA isolation. PCR confirmation of a proper CRE-lox recombination event is determined using the following primers (for BLoVeL-TSS based vectors):

Lox cassette forward:
[SEQ ID No. 51]
(AGCCGTGTAACCGAGCATAGtgaagcctgcttttttatactaacttgag cgaa)

Lox cassette reverse:
[SEQ ID No. 6]
(CTGTTTCCTTCAGCCTGCATGGCCTTGACTAGAGGGTCGACGG)

Those candidates showing a 462 bp product indicate a proper excision of the eGFP-BSR cassette whereas a 1,819 bp product indicates no excision occurred. Candidates with the correct PCR product are further tested by PCR to confirm the presence of the DNA elements of interest. Next, a second Nexus-TSS or BLoVeL-TSS vector containing a second variant of the lox sequence and a second DNA element can be loaded onto the chromosome using the same procedure as was used for loading the first DNA element.

Example 4: Alternative Iteration of Recyclable Drug Markers

In this example of recyclable drug markers, the lox variant sequences are incorporated into the GFP coding sequence at the N-terminal end behind the start codon. LoxP, lox 5171, lox 2272, and lox M2 sequences can encode, in the proper reading frame, small peptides that can be fused to reporter genes such as GFP. Thus, the resulting delivery vector places the attB sequence (used for targeting to the attP site on the synthetic platform chromosome (e.g. hSynC)) directly adjacent to the lox-GFP coding sequence.

LoxP Sequence:
[SEQ ID No. 7]
5' ATAACTTCGTATAATGTATGCTATACGAAGTTAT 3' loxP ORF (5'3' Frame 1):
[SEQ ID No. 7]
ataacttcgtataatgtatgctatacgaagttat

[SEQ ID No. 8]
I T S Y N V C Y T K L

Lox 5171 Sequence:
[SEQ ID No. 9]
ATAACTTCGTATAATGTgTaCTATACGAAGTTAT

Lox 5171 ORF (5'3' Frame 1):
[SEQ ID No. 9]
Ataacttcgtataatgtgtactatacgaagttat

[SEQ ID No. 10]
I T S Y N V Y Y T K L

Lox 2272 Sequence:
[SEQ ID No. 11]
ATAACTTCGTATAAaGTATcCTATACGAAGTTAT

Lox2272 (5'3' Frame 1):
[SEQ ID No. 11]
Ataacttcgtataaagtatcctatacgaagttat

[SEQ ID No. 12]
I T S Y K V S Y T K L

LoxM2 Sequence:
[SEQ ID No. 13]
ATAACTTCGTATAAgaaAccaTATACGAAGTTAT

LoxM2 (5'3' Frame 1):
[SEQ ID No. 13]
Ataacttcgtataagaaaccatatacgaagttat

[SEQ ID No. 14]
I T S Y K K P Y T K L

Figure 5:
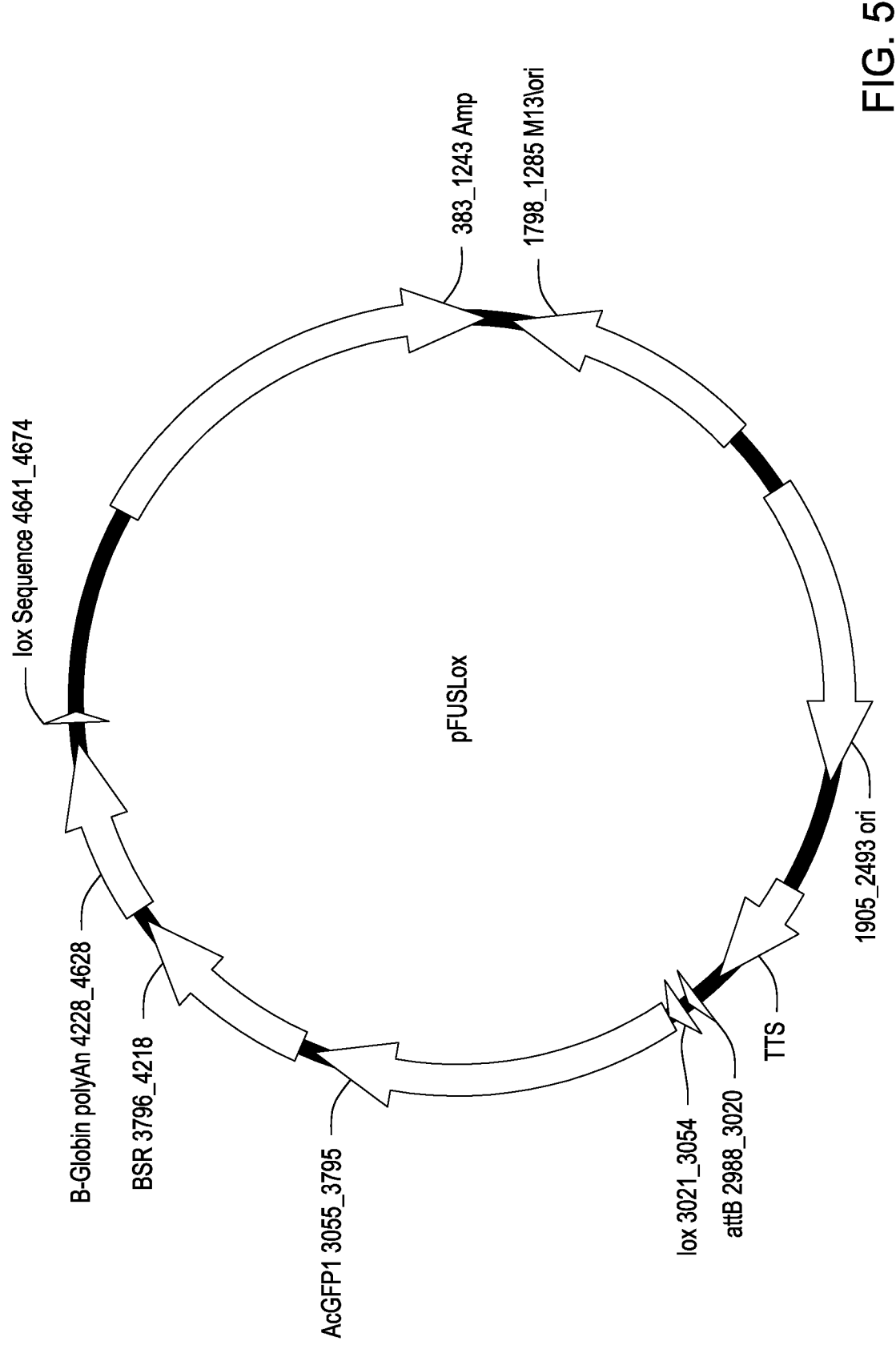
FIG. 5 is a map of the pFUSLox loading vector.

The lox-GFP fusion proteins are then attached to a second fragment encoding the blasticidin S resistance gene (BSR), polyA signal sequence, and a downstream lox sequence (or lox variant) in direct repeat orientation with respect to the upstream lox sequence incorporated into the GFP ORF. The order of the resulting recyclable drug cassette is as follows: attB-ATG-lox-GFP-BSR-polyA-lox-rest of vector. The resulting vector construct, pFUSLox, can then be utilized for targeting genes of interest onto the synthetic platform chromosome (e.g. hSynC). See FIG. 5.

Example 5: Delivery of pFUSLox with Gene of Interest onto hSynC Platform Using Lipofectamine LTX On day 0, HT1080 hSynC containing cells are seeded at $2 \times 10^5$ cells in one well of a 6-well dish in 2.5 ml of DMEM+10% FCIII serum+5 micrograms/ml Puromycin. On day 1, 1.25 micrograms of pFusLox containing the gene of interest are diluted into 500 microliters of Opti-MEM media without serum (Gibco). 1.25 microliters Plus Reagent (Thermo Fisher) is added to the tube, mixed gently, and incubated for 15 minutes at room temperature. 7.5 microliters of Lipofectamine LTX (Thermo Fisher) is added to the DNA/Plus Reagent tube, mixed gently, and incubated at room temperature for 25 minutes. The media is replaced with 2.5 ml DMEM+10% FCIII+Glutamax without antibiotics, and pFusLox/Opti-MEM/Plus Reagent/LTX is added to cells and the transfection reaction is incubated overnight in a 37° C., 5% $CO_2$ incubator. On day 2, the cells are harvested by trypsinization of transfected cells and resuspended in 3 ml DMEM+10% FCIII serum+3 micrograms/ml Puromycin. The cells are then applied to cell sorter and gate for GFP+ cells. A single cell sort for fluorescent cells is performed, and the single cell clones are expanded and delivery to the hSynC platform is confirmed by PCR analysis.

Example 6: Recycle Lox-GFP-BSR-polyA-Lox Cassette by Cre-Mediated Recombination On day 0, $2\times10^5$ hSynC/pFusLox engineered cells are seeded in one well of a 6-well dish in DMEM+10% FCIII serum+5 micrograms/ml Puromycin. On day 1, the cells are transfected with 1.25 micrograms of PSF-CMV-CRE-CRE Recombinase Expression Vector (Sigma Aldrich) vector utilizing the Lipofectamine LTX transfection reagent protocol as described above. The transfection reaction is then incubated for 24 hours in a 37° C., 5% $CO_2$ incubator. On day 2, the cells are harvested by trypsinization and resuspended in 3 ml DMEM+10% FCIII serum+3 micrograms/ml Puromycin. The cells are applied to cell sorter and gate for gfp− cells (nonfluorescent). A single cell sort or bulk sort for is performed for non-fluorescent cells. The single cell clones are expanded and delivery to hSynC platform is confirmed by PCR analysis.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, 16.

We claim:

1. A method for sequential loading of multiple nucleic acid sequences, each nucleic acid sequence containing at least one gene of interest onto an autonomously replicating nucleic acid sequence having multiple site-specific recombination target sites by removal and reuse of a single recyclable selectable marker gene cassette having an unlimited number of recyclings, the method comprising: in a population of animal or plant cells carrying the autonomously replicating nucleic acid sequence, using a first recombination system, to integrate a first delivery vector comprising a recyclable marker gene cassette and a first gene of interest into a first of the multiple site-specific recombination target sites on, the autonomously replicating nucleic acid sequence;

with a second recombination system and using signal sites alpha, excising the recyclable marker gene cassette from the autonomously replicating nucleic acid sequence, wherein the first gene of interest remains on the autonomously replicating nucleic acid sequence; identifying a first group of cells from the population, wherein the first gene of interest has been loaded onto the autonomously replicating nucleic acid sequence selectable and the recyclable marker gene cassette is no longer present; in the identified first group of cells, using the first recombination system, integrating to integrate a second delivery vector comprising the recyclable marker gene cassette and a second gene of interest into a second of the multiple site-specific recombination target sites on the autonomously replicating nucleic acid sequence; and with the second recombination system using signal sites beta, excising the recyclable marker gene cassette from the autonomously replicating nucleic acid sequence, wherein the second gene of interest remains on the autonomously replicating nucleic acid sequence.

2. The method of claim 1, further comprising the steps of:
   identifying a second group of cells in which the first and the second genes of interest have been loaded onto the autonomously replicating nucleic acid sequence and the recyclable marker gene cassette is no longer present;
   in the identified second group of cells, using the first recombination system, integrating a third delivery vector comprising the recyclable marker gene cassette and a third gene of interest into a third of the multiple recombination target sites on the autonomously replicating nucleic acid sequence; and with the second recombination system using signal sites gamma, excising the recyclable marker gene cassette from the autonomously replicating nucleic acid sequence wherein the third gene of interest remains on the autonomously replicating nucleic acid sequence.

3. The method of claim 1, wherein the autonomously replicating nucleic acid sequence is an endogenous chromosome.

4. The method of claim 1, wherein the autonomously replicating nucleic acid sequence is a synthetic chromosome.

5. The method of claim 4, wherein the synthetic chromosome is a mammalian synthetic chromosome.

6. The method of claim 5, wherein the synthetic chromosome is a human synthetic chromosome.

7. The method of claim 1, wherein the first recombination system is a Lambda integrase system.

8. The method of claim 1, wherein the second recombination system is a Cre/lox recombination system.

9. The method of claim 1, wherein the signal sites alpha and beta are selected from Lox2272, Lox5171, LoxM2 and LoxP, and the signal sites alpha and beta are not the same.

10. The method of claim 1, wherein the marker gene is a gene encoding for a fluorescent protein.

11. The method of claim 1, wherein each gene of interest is tagged with a different fluorescent marker.

12. A method for sequential loading of multiple nucleic acid sequences, each nucleic acid sequence containing at least one gene of interest, onto an autonomously replicating synthetic chromosome having multiple site-specific recombination target sites by removal and reuse of a single recyclable selectable marker gene cassette having an unlimited number of recyclings, the method comprising:
in a population of animal or plant cells carrying the autonomously replicating synthetic chromosome, using a first recombination system to integrate a first delivery vector comprising a recyclable marker gene cassette and a first gene of interest into a first of the multiple recombination target sites on the autonomously replicating synthetic chromosome;
with a second recombination system using signal sites alpha, excising the recyclable marker gene cassette from the autonomously replicating synthetic chromosome, wherein the first gene of interest remains on the autonomously replicating synthetic chromosome;
identifying a first group of cells from the population, wherein the first gene of interest has been loaded onto the autonomously replicating synthetic chromosome and the recyclable marker gene cassette is no longer present; in the identified first group of cells, using the first recombination system to integrate a second delivery vector comprising the recyclable marker gene cassette and a second gene of interest into a second of the multiple recombination target sites on the autonomously replicating synthetic chromosome; with the second recombination system using signal sites beta, excising the recyclable marker gene cassette from the autonomously replicating synthetic chromosome, wherein the second gene of interest remains on the autonomously replicating synthetic chromosome;
identifying a second group of cells in which the first and the second genes of interest have been loaded onto the autonomously replicating synthetic chromosome and the recyclable marker gene cassette is no longer present;
in the identified second group of cells, using the first recombination system to integrate a third delivery vector comprising the recyclable marker gene cassette and a third gene of interest into a third of the multiple site specific recombination target sites on the autonomously replicating synthetic chromosome; and with the second recombination system using signal sites gamma, excising the recyclable marker gene cassette from the autonomously replicating synthetic chromosome, wherein the third gene of interest remains on the autonomously replicating synthetic chromosome.

13. The method of claim 12, wherein the synthetic chromosome is a human synthetic chromosome.

14. The method of claim 12, wherein the first recombination system is a Lambda integrase system.

15. The method of claim 12, wherein the second recombination system is a Cre/lox recombination system.

16. The method of claim 12, wherein the signal sites alpha, beta, and gamma are selected from Lox2272, Lox5171, LoxM2 and LoxP, and each of signal sites alpha, beta, and gamma are distinct.

17. The method of claim 12, wherein the excising steps are performed by introduction of a nucleic acid vector encoding a second recombinase to the cell, introducing a second recombinase protein to the cell, or by delivering an encapsulated second recombinase to the cell.

18. The method of claim 17, wherein the excising steps are performed by introduction of a nucleic acid vector encoding the second recombinase to the cell.

19. The method of claim 12, further comprising determining whether the marker gene has been excised from the autonomously replicating synthetic chromosome by FACS sorting the cell after each excising step.

20. The method of claim 12, further comprising the steps of:
identifying a third group of cells in which the first, the second and the third genes of interest have been loaded onto the autonomously replicating synthetic chromosome and the recyclable marker gene cassette is no longer present;
in the identified third group of cells, using the first recombination system to integrate a fourth delivery vector comprising the recyclable marker gene cassette and a fourth gene of interest into a fourth of the multiple recombination target sites on the autonomously replicating synthetic chromosome; and
with the second recombination system using signal sites delta, excising the recyclable marker gene cassette from the autonomously replicating synthetic chromosome, wherein the fourth gene of interest remains on the autonomously replicating synthetic chromosome.

21. The method of claim 12, wherein each gene of interest is tagged with a different fluorescent marker.

* * * * *

```
                         SEQUENCE LISTING

<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: ligation junction

<400> SEQUENCE: 1
accgagctgc aagaactctt cctc                                            24

<210> SEQ ID NO 2
<211> LENGTH: 18
<212> TYPE: DNA
<213> ORGANISM: Artificial Sequence
<220> FEATURE:
<223> OTHER INFORMATION: ligation junction

<400> SEQUENCE: 2
ctcgccgcag ccgtgtaa                                                   18

<210> SEQ ID NO 3
<211> LENGTH: 22
<212> TYPE: DNA
<213> ORGANISM: Artificial Sequence
<220> FEATURE:
<223> OTHER INFORMATION: ligation junction

<400> SEQUENCE: 3
gcgctaatgc tctgttacag gt                                              22

<210> SEQ ID NO 4
<211> LENGTH: 20
<212> TYPE: DNA
<213> ORGANISM: Artificial Sequence
<220> FEATURE:
<223> OTHER INFORMATION: ligation junction

<400> SEQUENCE: 4
ggaaagctgc cagtgccttg                                                 20
```

```
<210> SEQ ID NO 5
<211> LENGTH: 53
<212> TYPE: DNA
<213> ORGANISM: Artificial Sequence
<220> FEATURE:
<223> OTHER INFORMATION: lox cassette

<400> SEQUENCE: 5
agccgtgtaa ccgagcatag tgaagcctgc tttttatac taacttgagc gaa        53

<210> SEQ ID NO 6
<211> LENGTH: 43
<212> TYPE: DNA
<213> ORGANISM: Artificial Sequence
<220> FEATURE:
<223> OTHER INFORMATION: lox cassette

<400> SEQUENCE: 6
ctgtttcctt cagcctgcat ggccttgact agagggtcga cgg                   43

<210> SEQ ID NO 7
<211> LENGTH: 34
<212> TYPE: DNA
<213> ORGANISM: Artificial Sequence
<220> FEATURE:
<223> OTHER INFORMATION: loxP

<400> SEQUENCE: 7
ataacttcgt ataatgtatg ctatacgaag ttat                             34

<210> SEQ ID NO 8
<211> LENGTH: 11
<212> TYPE: PRT
<213> ORGANISM: Artificial Sequence
<220> FEATURE:
<223> OTHER INFORMATION: loxP

<400> SEQUENCE: 8

Ile Thr Ser Tyr Asn Val Cys Tyr Thr Lys Leu
1               5                   10

<210> SEQ ID NO 9
<211> LENGTH: 34
<212> TYPE: DNA
<213> ORGANISM: Artificial Sequence
<220> FEATURE:
<223> OTHER INFORMATION: lox5171

<400> SEQUENCE: 9
ataacttcgt ataatgtgta ctatacgaag ttat                             34

<210> SEQ ID NO 10
<211> LENGTH: 11
<212> TYPE: PRT
<213> ORGANISM: Artificial Sequence
<220> FEATURE:
<223> OTHER INFORMATION: lox5171

<400> SEQUENCE: 10

Ile Thr Ser Tyr Asn Val Tyr Tyr Thr Lys Leu
1               5                   10

<210> SEQ ID NO 11
<211> LENGTH: 34
<212> TYPE: DNA
<213> ORGANISM: Artificial Sequence
<220> FEATURE:
```

```
<223> OTHER INFORMATION: lox2272

<400> SEQUENCE: 11
ataacttcgt ataaagtatc ctatacgaag ttat                              34

<210> SEQ ID NO 12
<211> LENGTH: 11
<212> TYPE: PRT
<213> ORGANISM: Artificial Sequence
<220> FEATURE:
<223> OTHER INFORMATION: lox2272

<400> SEQUENCE: 12

Ile Thr Ser Tyr Lys Val Ser Tyr Thr Lys Leu
1               5                   10

<210> SEQ ID NO 13
<211> LENGTH: 34
<212> TYPE: DNA
<213> ORGANISM: Artificial Sequence
<220> FEATURE:
<223> OTHER INFORMATION: loxM2

<400> SEQUENCE: 13
ataacttcgt ataagaaacc atatacgaag ttat                              34

<210> SEQ ID NO 14
<211> LENGTH: 11
<212> TYPE: PRT
<213> ORGANISM: Artificial Sequence
<220> FEATURE:
<223> OTHER INFORMATION: loxM2

<400> SEQUENCE: 14

Ile Thr Ser Tyr Lys Lys Pro Tyr Thr Lys Leu
1               5                   10
```